US010073028B2

(12) United States Patent
Cohen et al.

(10) Patent No.: US 10,073,028 B2
(45) Date of Patent: Sep. 11, 2018

(54) SPECTROMETER OPTICAL HEAD ASSEMBLY

(71) Applicant: SpectraSensors, Inc., Rancho Cucamonga, CA (US)

(72) Inventors: Joshua Cohen, Rancho Cucamonga, CA (US); Nathan St. John, Rancho Cucamonga, CA (US); Alfred Feitisch, Los Gatos, CA (US)

(73) Assignee: SpectraSensors, Inc., Rancho Cucamonga, CA (US)

( * ) Notice: Subject to any disclaimer, the term of this patent is extended or adjusted under 35 U.S.C. 154(b) by 243 days.

(21) Appl. No.: 14/842,642

(22) Filed: Sep. 1, 2015

(65) Prior Publication Data
US 2017/0059474 A1 Mar. 2, 2017

(51) Int. Cl.
G01N 21/01 (2006.01)
G01J 3/02 (2006.01)
G02B 7/02 (2006.01)
H01S 3/131 (2006.01)
H01S 5/00 (2006.01)
H01S 3/00 (2006.01)
G01N 21/27 (2006.01)
G02B 7/00 (2006.01)
(Continued)

(52) U.S. Cl.
CPC ............ *G01N 21/01* (2013.01); *G01J 3/0286* (2013.01); *G01J 3/42* (2013.01); *G01N 21/27* (2013.01); *G02B 7/008* (2013.01); *G02B 7/028* (2013.01); *H01S 3/0071* (2013.01); *H01S 3/1317* (2013.01); *H01S 5/0071* (2013.01); *H01S 5/06804* (2013.01); *G01N 2201/0231* (2013.01); *G01N 2201/0636* (2013.01)

(58) Field of Classification Search
CPC .......... G01J 3/0286; G01J 3/42; G01N 21/01; G01N 21/27; G01N 2201/0231; G01N 2201/0636; G02B 7/008; G02B 7/028; H01S 3/0071; H01S 3/1317; H01S 5/0071; H01S 5/06804
See application file for complete search history.

(56) References Cited

U.S. PATENT DOCUMENTS 2,541,437 A * 2/1951 Prescott ................. G01N 21/45
356/129
5,181,214 A * 1/1993 Berger .................... H01S 3/042
372/21
(Continued)

Primary Examiner — Gordon J Stock, Jr.
(74) Attorney, Agent, or Firm — Mintz Levin Cohn Ferris Glovsky and Popeo, P.C.

(57) ABSTRACT

An optical head assembly for use in a spectrometer is provided that is configured to characterize one or more constituents within a sample gas. The assembly includes a thermoelectric cooler (TEC) having a cold side on one end and a hot side on an opposite end, a cold plate in thermal communication with the cold side of the TEC, a hot block in thermal communication with the hot side of the TEC, a light source in thermal communication with the cold plate such that a change in temperature of the TEC causes one or more properties of the light source (e.g., wavelength, etc.) to change, and an optical element in thermal communication with the cold plate positioned to collimate light emitted by the light source through the sample gas (such that properties of the optical element vary based on a change in temperature of the TEC).

19 Claims, 5 Drawing Sheets

(51) Int. Cl.
   *H01S 5/068*       (2006.01)
   *G01J 3/42*        (2006.01)

(56) References Cited

U.S. PATENT DOCUMENTS

| | | | | |
|---|---|---|---|---|
| 5,265,115 A | * | 11/1993 | Amano | H01S 3/1312 |
| | | | | 372/34 |
| 5,267,252 A | * | 11/1993 | Amano | H01S 3/042 |
| | | | | 372/34 |
| 5,283,695 A | * | 2/1994 | Ziph-Schatzberg | |
| | | | | G02B 6/4204 |
| | | | | 359/220.1 |
| 5,341,388 A | * | 8/1994 | Masuda | H01S 3/042 |
| | | | | 372/34 |
| 5,446,750 A | * | 8/1995 | Ohtsuka | H01S 3/025 |
| | | | | 372/22 |
| 5,832,015 A | * | 11/1998 | Goto | H01S 3/025 |
| | | | | 372/34 |
| 7,586,094 B2 | | 9/2009 | Liu et al. | |
| 7,704,301 B2 | | 4/2010 | Zhou et al. | |
| 8,164,748 B1 | | 4/2012 | Flanders et al. | |
| 2007/0047599 A1 | | 3/2007 | Wysocki et al. | |
| 2010/0200728 A1 | * | 8/2010 | Ingber | G01J 1/32 |
| | | | | 250/205 |
| 2013/0003045 A1 | * | 1/2013 | Wilkins | G01J 3/42 |
| | | | | 356/51 |
| 2013/0286397 A1 | | 10/2013 | Witinski et al. | |

\* cited by examiner

SPECTROMETER OPTICAL HEAD ASSEMBLY

TECHNICAL FIELD

The subject matter described herein relates to an optical head assembly for use with a spectrometer that comprises a hot block in thermal communication with a hot side of a thermoelectric cooler (TEC) and a cold plate in thermal communication with the cold side of the TEC as well as a light source and an optical element.

BACKGROUND

Beam pointing stability is critical to maintaining a calibration state of a spectrometer and laser power impinging upon an optical detector within spectrometers that utilize lasers, such as tunable diode lasers (TDL), as their light sources. Optical elements, such as laser lenses, are often used to steer beams emitted by the lasers along a particular beam path within a sample cell for detection by a detector. However, fluctuations in ambient temperatures can cause the thermal expansion of a laser lens mounting fixture to change the relative alignment of the laser lens to the laser, which, in turn, has a negative impact on laser beam alignment stability. These temperature fluctuations are particularly problematic in typical spectrometer field installations, especially in climates having large temperature swings such as deserts and the like.

Additionally, especially for TDL spectrometers requiring short focal length lenses, the temperature of the laser lens can influence the temperature of the laser, causing a wavelength shift with ambient temperature, also known as laser drift, which can result in an offset from the state of calibration of the spectrometer. In a typical application, such as described in co-owned US patent (insert reactive gas patent number for differential spectroscopy) such detrimental laser wavelength shifts can occur with laser temperature changes in the order of single digit mK. This thermal influence on the TDL is typically undetected by the temperature sensor used to control the laser set-point temperature, making it impossible to correct with a controller.

SUMMARY

In a first aspect, an optical head assembly for use in a spectrometer is provided that is configured to characterize one or more constituents within a sample gas. The assembly includes a thermoelectric cooler (TEC) having a cold side on one end and a hot side on an opposite end, a cold plate in thermal communication with the cold side of the TEC, a hot block in thermal communication with the hot side of the TEC, a light source in thermal communication with the cold plate such that a change in temperature of the TEC causes one or more properties of the light source to change, and an optical element in thermal communication with the cold plate positioned to collimate light emitted by the light source through the sample gas (such that properties of the optical element vary based on a change in temperature of the TEC).

The following variations can be used in combination or singly depending on the desired configuration.

The optical element can be coupled to the cold plate by a lens mount.

The assembly can include a detector in thermal communication with the cold plate positioned to detect light emitted by the light source after passing through the optical element. In some variations, a detector lens can also be provided that is in thermal communication with the cold plate positioned such that light emitted by the light source passes through both the optical element and the detector lens prior to being detected by the detector. In some variations, an optical element sliding plate in thermal communication with the cold plate can be provided that is configured to secure and selectively move the optical element in at least one dimension to allow the optical element to align a beam path between the light source and the detector.

The detector can take various forms including one or more of: an indium gallium arsenide (InGaAs) detector, an indium arsenide (InAs) detector, an indium phosphide (InP) detector, a silicon (Si) detector, a silicon germanium (SiGe) detector, a germanium (Ge) detector, a mercury cadmium telluride detector (HgCdTe or MCT), a lead sulfide (PbS) detector, a lead selenide (PbSe) detector, a thermopile detector, a multi-element array detector, a single element detector, a photo-multiplier, a complementary metal oxide semiconductor (CMOS) detector, a charge coupled device (CCD) detector, a photodiode, a photodetector, or a photoacoustic detector.

The assembly can include a temperature sensor in thermal communication with the cold plate or the light source and at least one remote temperature controller.

The cold plate and the hot block can be both bonded to the TEC by at least one of a bonding epoxy, metallic solder, laser sintering, mechanical clips, spring force elements, van der Waals forces, metal interdiffusion, or mounting screws.

The cold plate can envelop the light source on at least two sides (e.g., four sides).

The hot block can include a first portion substantially parallel to the hot side of the TEC and at least two arms extending from opposing ends of the first portion towards the cold side of the TEC that are substantially perpendicular to the hot side of the TEC.

The cold plate can be a unitary piece of material or it can comprise multiple pieces of coupled material. Similarly, the hot block can be a unitary piece of material or it can comprise multiple pieces of coupled material. Sample materials include, but are not limited to, metal, ceramic, glass, grown crystal, semiconductor materials, composites, and the like.

The optical element can be a collimating lens. In other variations, the optical element can be one or more of: a diffractive optical element, a transmissive optical element, a reflective optical element a waveguide optical element, a holographic optical element, an acousto-optic element, an electro-optic element, a semiconductor optical element, a volume phase grating optical element, an optical fiber, a hollow core light guide, a solid core light guide, a prism, a diffuser, an aperture, a beam splitter, or a beam combiner.

The light source can include one or more light sources selected from a group consisting of: a tunable diode laser, a semiconductor laser, a semiconductor optical amplifier, a quantum cascade laser, an intra band cascade laser, a horizontal cavity emitting laser, a vertical cavity surface emitting semiconductor laser, a distributed feedback laser, a distributed Bragg reflector laser, an amplified distributed feedback laser, an amplified distributed Bragg reflector laser, a multi-element grating coupled distributed feedback laser, a multi-element grating coupled distributed Bragg reflector semiconductor laser, a gas discharge laser, a liquid laser, a solid state laser, a diode pumped solid state laser, a fiber laser, a sum frequency mixing non-linear optical process, a difference frequency mixing non-linear optical process, an optical parametric oscillator, an external cavity diode laser, an extended cavity diode laser, a light emitting diode, an amplified spontaneous emission source, a super-continuum optical source, or a lamp.

In an interrelated aspect, a spectrometer is provided that includes a thermoelectric cooler (TEC), a cold plate, a hot block, a light source, an optical element, a controller, and a detector. The TEC has a cold side on one end and a hot side on an opposite end. The cold plate is in thermal communication with the cold side of the TEC. The hot block is in thermal communication with the hot side of the TEC. The light source is in thermal communication with the cold plate such that a change in temperature of the TEC causes one or more properties of the light source to change. The properties can include, for example, wavelength and/or lasing efficiency. Increasing quantum well temperature reduces lasing efficiency of a semiconductor laser and thus output power at constant operating current. Quantum well temperature depends upon the cold plate temperature, resistive heat generation from injection current and on ambient heating (mostly convection and radiation on the p-side).

The optical element is in thermal communication with the cold plate and is positioned to collimate light emitted by the light source through the sample gas (such that properties of the optical element vary based on a change in temperature of the TEC). The controller is coupled to the TEC and/or the light source. The detector is positioned to detect light emitted by the light source after passing through the optical element and the sample gas.

The current subject matter provides many technical advantages. For example, the current subject matter allows for the reduction of thermal-based wavelength shift of lasers forming parts of spectrometers. Further, the current subject matter is advantageous in that it enables improved laser beam pointing stability by eliminating thermal expansion distortions to the laser lens position relative to the laser. Moreover, the current subject matter, by providing temperature stabilized optics helps improve wavelength stability against ambient temperature changes and thus measurement accuracy and fidelity of a concentration measurement with respect to the state of calibration of a TDL spectrometer due to the optics being very close to the laser ridge and quantum well. Yet further, the current subject matter is advantageous in that it allows for more precise spectroscopy with less overall thermal control of the spectrometer temperature with respect to an optical head assembly. In addition, the designs provided herein can be made in a cost-effective manner using fewer parts and which can be varied in size and shape depending on the desired application.

The details of one or more variations of the subject matter described herein are set forth in the accompanying drawings and the description below. Other features and advantages of the subject matter described herein will be apparent from the description and drawings, and from the claims.

DESCRIPTION OF DRAWINGS

Like reference symbols in the drawings indicate like elements.

DETAILED DESCRIPTION

The current subject matter describes a tunable diode laser absorption spectroscopy (TDLAS) optical head assembly with a collimating laser lens, used for beam steering, mounted in such a way as to be in thermal equilibrium with a tunable diode laser (TDL). This lens mounting configuration puts the TDL, the detector and both lenses in a thermally stabilized state to prevent them from being influenced by ambient temperatures. With all optical components in thermal equilibrium there is negligible differential thermal expansion, preventing misalignment. Furthermore, there is no ambient temperature influence to the TDL through the lens because they are always maintained at the same relative temperature. It will be appreciated that, while the current subject matter describes a particular type of spectrometer and a particular type of light source as examples, the principles described herein are applicable to other types of spectrometers and light sources in which thermal equilibrium is beneficial.

Figure 1:
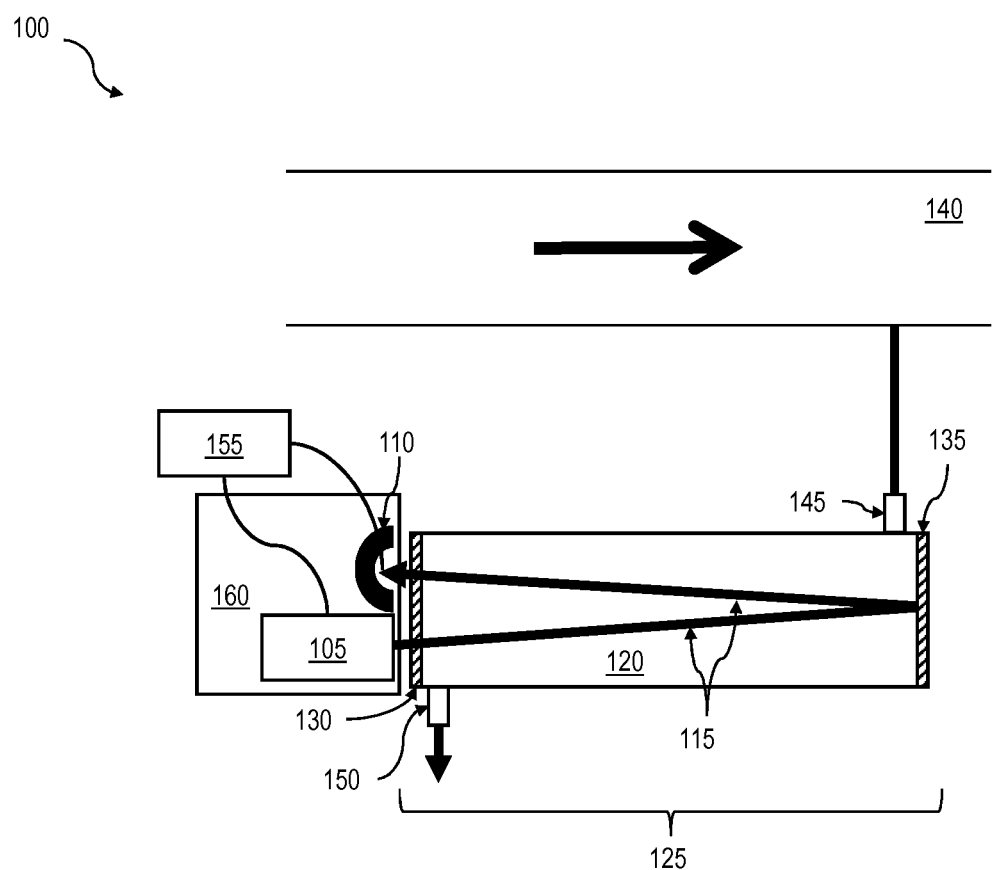
FIG. 1 is a diagram illustrating a closed path spectrometer having an optical head assembly.
Figure 2:
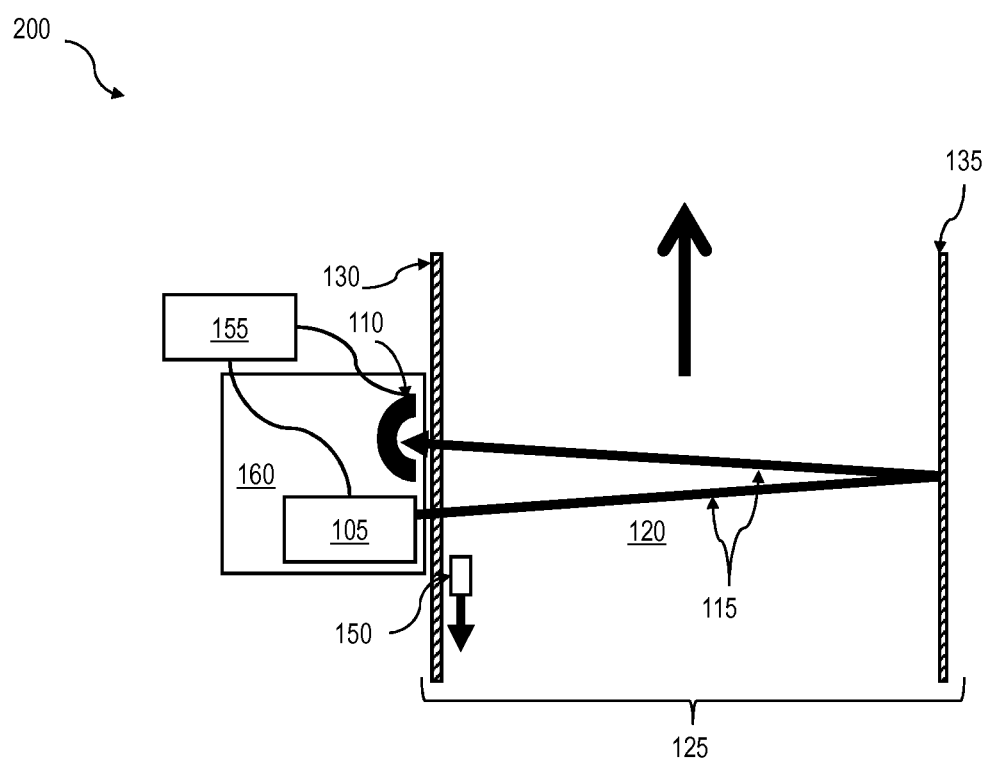
FIG. 2 is a diagram illustrating an open path spectrometer having an optical head assembly.

FIGS. 1 and 2 are diagrams 100, 200 that show example spectrometers for implementing the current subject matter. While the following is described in connection with detecting absorbing media within gas, it will be appreciated that the current subject matter can also be applied to detecting absorbing media within liquid. The subject matter described herein can be and/or form part of a spectroscopic analysis system that includes any of an absorption spectroscopic analysis system, an emission spectroscopic analysis system, a fluorescence spectroscopic analysis system, a Fourier transform infrared spectroscopic analysis system, a non-dispersive infrared (NDIR) spectroscopic analysis system, a cavity enhanced spectroscopic analysis system, a cavity ring-down spectroscopic (CRDS) analysis system, an integrated cavity output spectroscopic (ICOS) analysis system, a photoacoustic spectroscopic analysis system, and a Raman spectroscopic analysis system.

In some cases, a spectrometer measures light reflected off a surface (for example in a sample cell, etc.). Such a spectrometer can take various forms including, for example, a Herriott Cell, an off-axis optical resonator, an on-axis optical resonator, an elliptical light collector, a White cell, a spheroidal cell, a non-Herriott longitudinal flow sample call, a toroidally or spheroidally shaped transverse flow cell and the like, an optical cavity, a hollow core light guide, a multiple pass configuration in which the light beam is reflected at least once or a single pass configuration in which the light is not being reflected while the light traverses the sample cell (in such cases, as described further below, the detector 110, the detector lens mount 345 and the detector optical element 340 would not form part of the optical head assembly 160).

In other variations, as illustrated in FIG. 2 the current subject matter can be part of an open path system that does not include a dedicated sample cell. While the variation illustrated in FIG. 2 includes a reflector/reflective surface 135, it can be appreciated that the current subject matter is also applicable to cross-stack/cross-pipe arrangements in which the light source 105 is opposite the detector 110 (and the stack/pipe can include opposing windows through which the emitted light passes).

Such open path systems can be used for various applications including atmospheric pollutant studies, fence line monitoring, tank blanketing, process line/tank leak detection, industrial gas-purity applications, and monitoring and control of combustion processes, especially on exhaust stacks. Cross-path systems can be used for applications such as detection of potential explosion hazards.

A light source 105 can provide continuous or pulsed light that is directed to a detector 110 via a path length 115. The light source 105 can form part of an optical head assembly 160. In some variations, the optical head assembly 105 also includes the detector (as illustrated in FIG. 1).

The light source 105 can include, for example, one or more of a tunable diode laser, a semiconductor laser, a semiconductor optical amplifier, a quantum cascade laser, an intra band cascade laser, a horizontal cavity laser, a vertical cavity surface emitting semiconductor laser, a distributed feedback laser, a distributed Bragg reflector laser, an amplified distributed feedback laser, an amplified distributed Bragg reflector laser, a multi-element grating coupled distributed feedback laser, a multi-element grating coupled distributed Bragg reflector semiconductor laser, a gas discharge laser, a liquid laser, a solid state laser, a diode pumped solid state laser, a fiber laser, a sum frequency mixing non-linear optical process, a difference frequency mixing non-linear optical process, an optical parametric oscillator, an external cavity diode laser, an extended cavity diode laser, a light emitting diode, an amplified spontaneous emission source, a super-continuum optical source, a lamp, and the like. The light source 105 can be of a non-laser light type and can include one or more of a light emitting diode (LED), a lamp, and/or another device capable of generating frequency tunable light through nonlinear optical interactions and/or through spectral filtering. Examples of lamps can include, but are not limited to thermal sources, discharge sources, laser assisted or laser driven plasma sources, fluorescent sources, super-luminescent sources, amplified spontaneous emission (ASE) sources, super-continuum sources, and spectrally broad sources, and the like.

The detector 110 can include, for example, an indium gallium arsenide (InGaAs) detector, an indium arsenide (InAs) detector, an indium phosphide (InP) detector, a silicon (Si) detector, a silicon germanium (SiGe) detector, a germanium (Ge) detector, a mercury cadmium telluride detector (HgCdTe or MCT), a lead sulfide (PbS) detector, a lead selenide (PbSe) detector, a thermopile detector, a multi-element array detector, a single element detector, a photomultiplier, a complementary metal oxide semiconductor (CMOS) detector, a charge coupled device (CCD) detector, a photodiode, a photodetector, a photoacoustic detector, and the like.

The path length 115 can traverse one or more volumes. In the example shown in FIG. 1, the path length 115 can twice traverse a volume 120 of an optical cell 125 that includes a window or other at least partially radiation transmissive surface 130 and at least one reflector (e.g., a mirror, etc.) 135 or other at least partially radiation reflective surface 135 that at least partially defines the volume 120. The at least one reflector 135 can be a mirror, a corner cube retro-reflector, a multiple reflection light routing prism and the like. The at least one surface 135 and/or multiple surfaces of the reflector can be of infinite radius of curvature, positive radius of curvature, negative radius f curvature, parabolic surface shape, elliptical surface shape, hyperbolic surface shape, cylindrical surface shape, spherical surface shape, random surface shape and the like. The at least one reflecting surface 135 can be made from metal, glass, ceramic, semiconductor material, composites, alloys, dielectric material, multiple layers of dielectric material and the like.

Sample gas can, in some implementations, be obtained from a gas source, which in the examples of FIG. 1 is a pipeline 140, for delivery to the volume 120, for example via a sample extraction port or valve 145 that receives the sample gas from the source. Gas in the volume 120 can exit via a second outlet valve or port 150.

A controller 155, which can include one or more programmable processors or the like, can communicate with one or more of the light source 105 and the detector 110 for controlling the emission of the light 115 and receiving signals generated by the detector 110 that are representative of the intensity of light impinging on the detector 110 as a function of wavelength. In various implementations, the controller 155 can be a single unit that performs both of controlling the light source 105 and receiving signals from the detector 110, or it can be more than one unit across which these functions are divided. Communications between the controller 155 or controllers and the light source 105 and detector 110 can be over wired communications links, wireless communications links, or any combination thereof. The controller 155 can also, in some cases, be used to quantify an amount of absorbing media using the signal generated by the detector 110. In other variations, the quantification can be determined by at least one remote data processor.

The volume 120 can be maintained at a stable temperature and pressure. Alternatively, the volume 120 can include one or more temperature and/or pressure sensors to determine a current temperature and pressure within that volume for use in one or more calculations to compensate for temperature and/or pressure changes relative to a validation or calibration condition of the spectroscopic instrument. In some cases, such sensors can form part of or be coupled to the optical head assembly 160. Furthermore, the volume 120 can be adjusted to preset temperature and pressure by heating elements and pressure control elements or mass flow controllers.

The controller 155, or alternatively one or more other data processors that are either collocated with the other components or in wireless, wired, etc. communication therewith.

Figure 3:
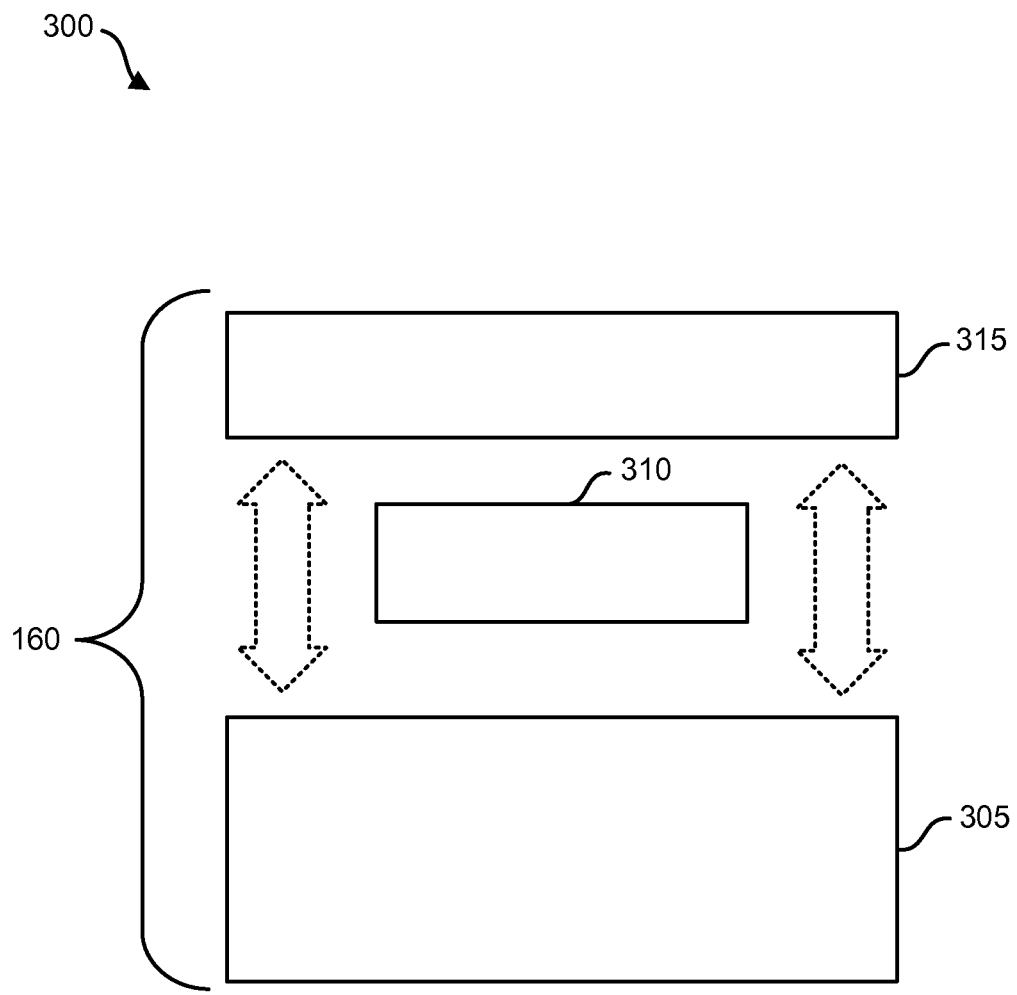
FIG. 3 is a block diagram illustrating a subsection of an optical head assembly having a TEC with a hot block on a hot side and a cold plate on the cold side.

FIG. 3 is a block diagram 300 illustrating a subsection of the optical head assembly 160 that includes a hot block 305, a thermoelectric cooler (TEC) 310, and a cold plate 315. The hot block 305 is in thermal communication (either directly or indirectly via one or more heat transfer elements) with a hot side of the TEC 310 and the cold plate 315 is in thermal communication (either directly or indirectly via one or more heat transfer elements) with a cold side of the TEC 310. The arrows in FIG. 3 represent the flow of heat. In some variations, one or more of the hot block 305 and the cold plate 315 can be made from a unitary piece of material such as metal, ceramic, glass, composite or the like thermally conductive material while, in other cases, one or both of the hot block 305 and the cold plate 315 comprise multiple components, made from at least one of a metal (e.g., aluminum, etc.), an alloy, a powder sinter material (e.g., aluminum, CuW sinter metal, etc.), a ceramic (e.g., BeO ceramic, etc.), glass, grown crystal, a semiconductor, or a composite (e.g., Cu:diamond, etc.) or like thermally conductive material, in thermal communication (and configured to transfer heat). In some variations.

Still further, both the hot block 305 and cold plate 315 can be made of varying geometries. For example, the hot block 305 can, in some variations, include mounting and heat-sinking legs that provide for a rigid mounting surface for the remainder of the optical system while, at the same time, assisting in heat removal from the hot side of the hot block.

The cold plate 315 and the heat sink 305 can be bonded to the TEC 310 using an epoxy or a metallic solder having good thermal conductivity as well as exceptional strength. With the current application, mechanical stability can be more important than thermal conductivity because the application may not require fast, dynamic cooling of the cold plate 315 and because the epoxy bond line is minimized using an applied compression force during the epoxy cure period. To achieve exceptional strength of the bond line it is beneficial to have good adhesion to the cold plate 315 and heat block 305 surfaces (typically a very thermally conductive metal such as aluminum). Bonding the TEC 310 with a metallic solder has similar mechanical strengths but can require varied baking and soldering processes to achieve as strong a bond line as possible. Such processes may also be referred to as optical contacting or as diffusion bonding. In still other variations, one or more of the cold plate 315 and the heat sink 305 can be secured to the TEC 310 using one or more mounting screws, mechanical clips, van der Waals forces, metal layer inter-diffusion and/or spring force elements. The use of van der Waals forces, in particular, can eliminate the use of an epoxy, metal or other filler material, achieving good heat transfer and mechanical strength by bringing two surfaces in close enough contact for molecular force interaction.

Figure 4:
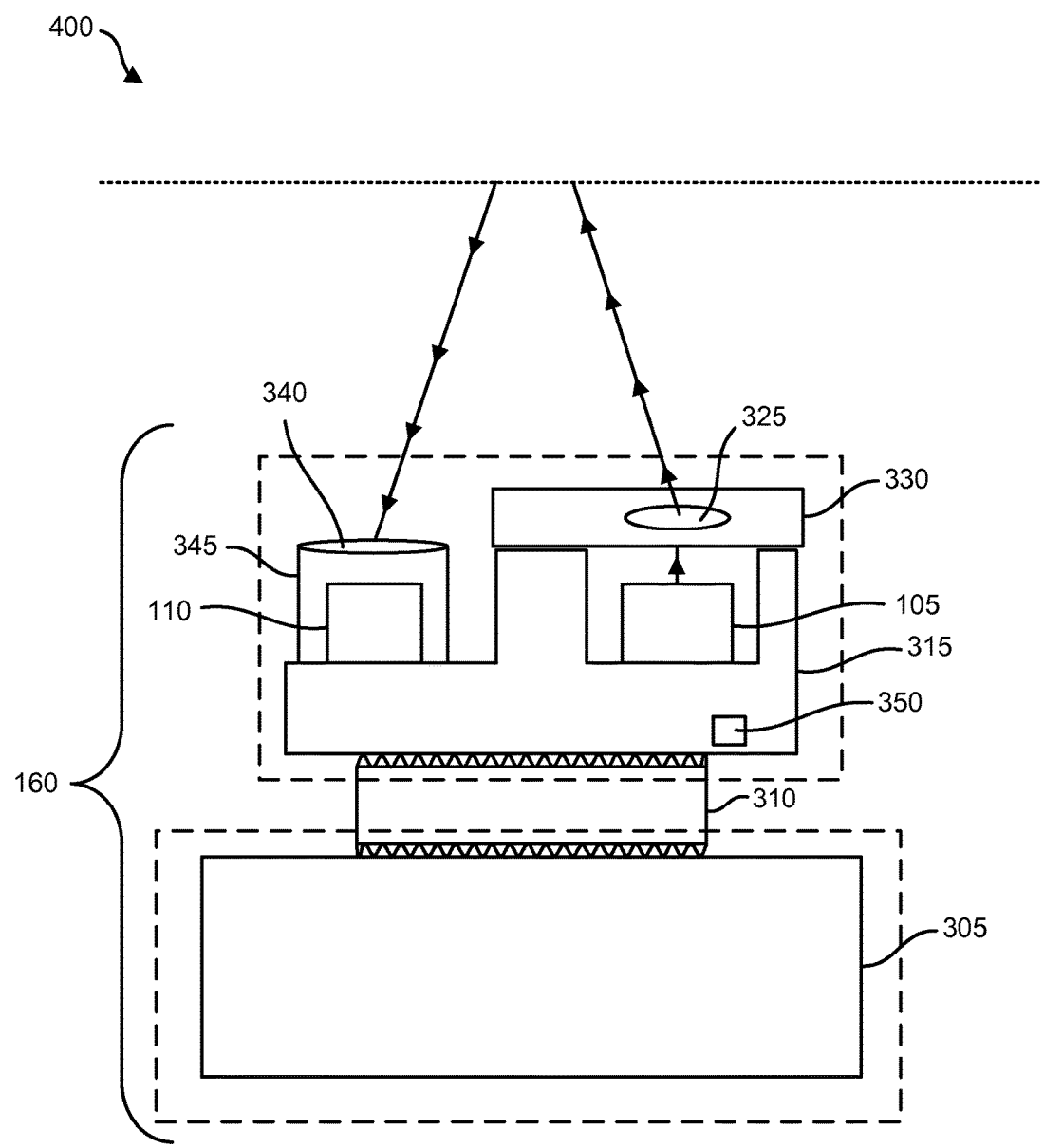
FIG. 4 is a block diagram illustrating a cross section of an optical head assembly.

FIG. 4 is a block diagram 400 illustrating further elements of the optical head assembly 160. As illustrated, the cold plate 315 can have a shape to enable it to act as a component workbench that in turn forms part of the optical head assembly. The light source 105 can be positioned to emit light through an optical element 325 which, in turn, is mounted on or otherwise affixed by a structure element 330 (which is also illustrated in diagram 400 of FIG. 4). The optical element 325 can be used to steer the beam such that it has a desired shape and spatial direction. In some variations, the optical element 325 can be a collimating lens. In other variations, the optical element 325 can be one or more of: a diffractive optical element, a transmissive optical element, a reflective optical element a waveguide optical element, a holographic optical element, an acousto-optic element, an electro-optic element, a semiconductor optical element, a volume phase grating optical element, an optical fiber, a hollow core light guide, a solid core light guide, a prism, a diffuser, an aperture, a beam splitter, or a beam combiner.

The cold plate 315 can, in some cases, envelop or otherwise shield two or more sides/faces of the light source 105. FIG. 4 illustrates a beam path from the light source 105 that is shaped and directed by the optical element 325 and which is reflected back (not shown) to the detector lens 340 which in turn focuses/shapes the beam for detection by the detector 110.

Figure 5:
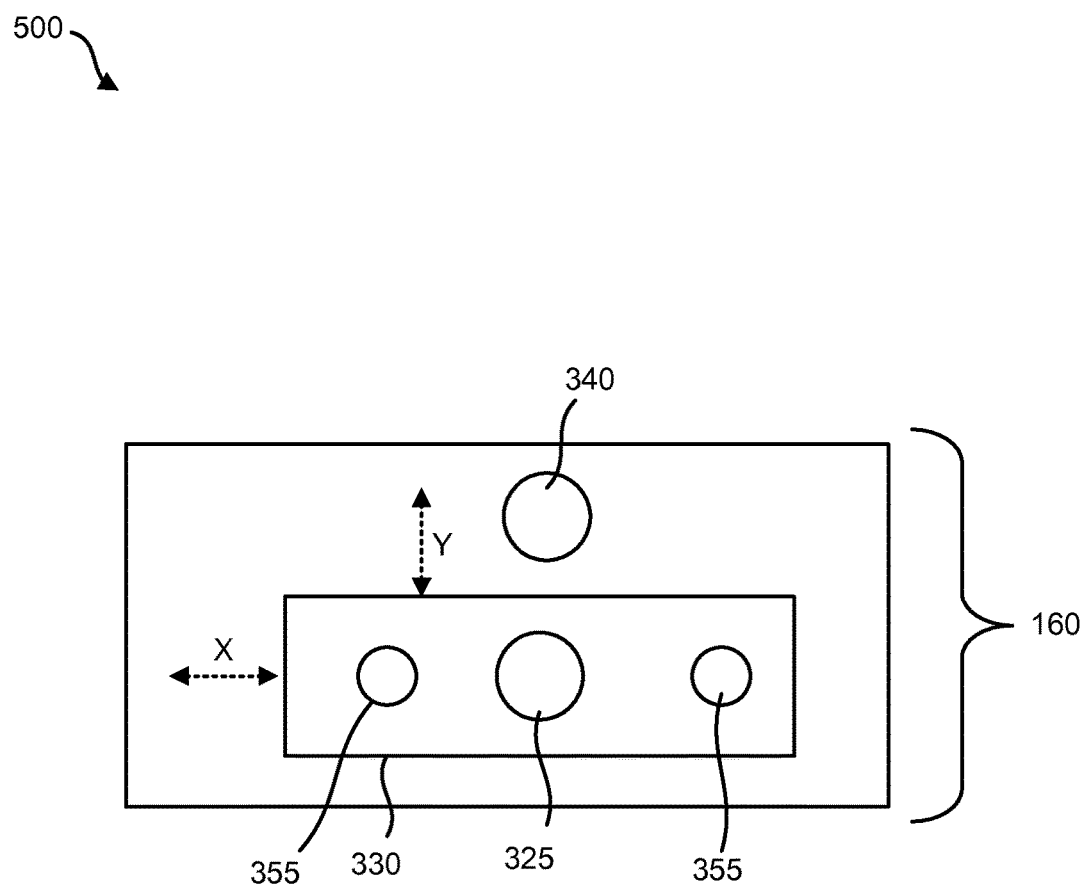
FIG. 5 is a block diagram illustrating a top view of an optical head assembly with arrows indicating directions in which a structure element can be move.

The structure element 330 can either be part of the cold plate 315 or it can be one or more components coupled thereto (and in thermal communication). In some variations, the structure element 330 includes mounting holes 355 (illustrated in diagram 500 of FIG. 5) which can be used to secure the structure element 330 to the cold plate 315. The structure element 330 can include, for example, one or more slider elements to alter the X and Y position of the optical element 325 in relation to the light source 105 to allow for beam pointing an alignment (as shown in dashed lines). In some variations, the structure element 330 can include threading that allows the optical element 325 be threaded in or out to adjust beam focus. In addition, the optical element 325 can be in thermal communication with the cold plate 315 via the structure element 330.

The optical head assembly 160 can also include the detector 110 that is in thermal communication with the cold plate 315. The detector 110 can be mounted to or affixed to the cold plate 315 by a detector lens mount 345 which, in turn, can secure a detector lens 340. The detector lens mount 345 can include a threaded portion to allow the focus of a detector lens 340 to be adjusted (by changing the position of the detector lens 340 in relation to the detector 335). In other variations, the detector lens 340 can be fixedly secured (e.g., bonded, etc.) to the detector lens mount 345.

The optical head assembly 160 can also include a temperature sensor 350 (e.g., thermistor, etc.) that is used to calculate a temperature of the light source 105 which can be used to determine whether or not to change one or more operating parameters of the light source 105. The temperature sensor 350 can be enclosed or otherwise in thermal communication with the cold plate 315 or light source 105 to sense as accurate a temperature as possible of the light source 105. To more effectively isolate the light source 105 from ambient temperature variations, conductive heat paths between the cold plate 315 and the hot block 305, or between other components in thermal communication with ambient temperature can be eliminated. In such a configuration (and as illustrated in FIG. 3), the only ambient influences on the optical components are through natural convection through the enclosed space of the optical head. Such an implementation can require the TEC 310 itself to maintain the mechanical mounting position of all of the optical components relative to the sample cell assembly. In some variations, the TEC 310 can be filled with a potting material which eliminates moisture intrusion and dramatically increases the strength of the TEC 310 under shear load.

Additionally, the cold plate 315 on the cold side of the TEC 310 can, in some variations, be insulated from ambient air natural convection to add additional thermal isolation with respect to ambient temperature.

In the descriptions above and in the claims, phrases such as "at least one of" or "one or more of" may occur followed by a conjunctive list of elements or features. The term "and/or" may also occur in a list of two or more elements or features. Unless otherwise implicitly or explicitly contradicted by the context in which it is used, such a phrase is intended to mean any of the listed elements or features individually or any of the recited elements or features in combination with any of the other recited elements or features. For example, the phrases "at least one of A and B;" "one or more of A and B;" and "A and/or B" are each intended to mean "A alone, B alone, or A and B together." A similar interpretation is also intended for lists including three or more items. For example, the phrases "at least one of A, B, and C;" "one or more of A, B, and C;" and "A, B, and/or C" are each intended to mean "A alone, B alone, C alone, A and B together, A and C together, B and C together, or A and B and C together." In addition, use of the term "based on," above and in the claims is intended to mean, "based at least in part on," such that an unrecited feature or element is also permissible.

The subject matter described herein can be embodied in systems, apparatus, methods, and/or articles depending on the desired configuration. The implementations set forth in the foregoing description do not represent all implementations consistent with the subject matter described herein. Instead, they are merely some examples consistent with aspects related to the described subject matter. Although a few variations have been described in detail above, other modifications or additions are possible. In particular, further features and/or variations can be provided in addition to those set forth herein. For example, the implementations described above can be directed to various combinations and subcombinations of the disclosed features and/or combinations and subcombinations of several further features disclosed above. In addition, the logic flows depicted in the accompanying figures and/or described herein do not necessarily require the particular order shown, or sequential order, to achieve desirable results. Other implementations may be within the scope of the following claims.

What is claimed is:

1. An optical head assembly for use in a spectrometer that is configured to characterize one or more constituents within a sample gas, the assembly comprising:
   a thermoelectric cooler (TEC) having a cold side on one end and a hot side on an opposite end;
   a cold plate in thermal communication with the cold side of the TEC;
   a hot block in thermal communication with the hot side of the TEC;
   a light source in thermal communication with the cold plate such that a change in temperature of the TEC causes one or more properties of the light source to change, the cold plate enveloping the light source on at least two sides; and
   an optical element in thermal communication with the cold plate positioned to collimate light emitted by the light source through the sample gas, wherein properties of the optical element vary based on a change in temperature of the TEC.

2. The assembly of claim 1, wherein the optical element is coupled to the cold plate by a lens mount.

3. The assembly of claim 1 further comprising: a temperature sensor in thermal communication with the cold plate or the light source and at least one remote temperature controller.

4. The assembly of claim 1, wherein the cold plate comprises a unitary piece of a single material.

5. The assembly of claim 1, wherein the hot block comprises a unitary piece of material.

6. The assembly of claim 1, wherein the optical element is a collimating lens.

7. The assembly of claim 1, wherein the light source comprises a laser.

8. The assembly of claim 1 further comprising:
   a detector in thermal communication with the cold plate positioned to detect light emitted by the light source after passing through the optical element.

9. The assembly of claim 8 further comprising:
   a detector lens in thermal communication with the cold plate positioned such that light emitted by the light source passes through both the optical element and the detector lens prior to being detected by the detector.

10. The assembly of claim 9 further comprising:
    an optical element sliding plate in thermal communication with the cold plate configured to secure and selectively move the optical element in at least one dimension to allow the optical element to align a beam path between the light source and the detector.

11. A spectrometer comprising:
    a thermoelectric cooler (TEC) having a cold side on one end and a hot side on an opposite end;
    a cold plate in thermal communication with the cold side of the TEC;
    a hot block in thermal communication with the hot side of the TEC;
    a light source in thermal communication with the cold plate such that a change in temperature of the TEC causes one or more properties of the light source to change, the cold plate enveloping the light source on at least two sides; and
    an optical element in thermal communication with the cold plate positioned to collimate light emitted by the light source through the sample gas, wherein properties of the optical element vary based on a change in temperature of the TEC;
    a controller coupled to the TEC and/or the light source; and
    a detector positioned to detect light emitted by the light source after passing through the optical element and the sample gas.

12. The spectrometer of claim 11 further comprising:
    a temperature sensor in thermal communication with the cold plate or the light source and at least one remote temperature controller.

13. The spectrometer of claim 11, wherein the detector is positioned on an opposing cross-stack or cross-pipe surface relative to the light source.

14. The spectrometer of claim 11, wherein the light source comprises a laser.

15. The spectrometer of claim 11 further comprising:
    at least one reflective surface positioned to reflect light emitted by the light source so that it can be detected by the detector.

16. The spectrometer of claim 11, wherein the detector is in thermal communication with the cold plate, wherein properties of the detector vary based on a change in temperature of the TEC.

17. The spectrometer of claim 15, wherein the at least one reflective surface forms part of a sample cell.

18. The spectrometer of claim 16 further comprising:
    a detector lens in thermal communication with the cold plate positioned such that light emitted by the light source passes through both the optical element and the detector lens prior to being detected by the detector, wherein properties of the detector lens vary based on a change in temperature of the TEC.

19. The spectrometer of claim 18 further comprising:
    an optical element sliding plate in thermal communication with the cold plate configured to secure and selectively move the optical element in at least on dimension to allow the optical element to be align a beam path between the light source and the detector.

* * * * *